(12) United States Patent
Leblanc et al.

(10) Patent No.: US 9,079,897 B2
(45) Date of Patent: Jul. 14, 2015

(54) IMIDAZO-PYRIDINE DERIVATIVES AS ACTIVIN-LIKE RECEPTOR KINASE (ALK4 OR ALK5) INHIBITORS

(75) Inventors: Catherine Leblanc, West Sussex (GB); Cathy Ritchie, Hants (GB); Duncan Shaw, West Sussex (GB); Nikolaus Johannes Stiefl, Lörrach (DE)

(73) Assignee: NOVARTIS AG, Basel (CH)

( * ) Notice: Subject to any disclaimer, the term of this patent is extended or adjusted under 35 U.S.C. 154(b) by 426 days.

(21) Appl. No.: 12/935,405

(22) PCT Filed: Apr. 27, 2009

(86) PCT No.: PCT/EP2009/055066
§ 371 (c)(1),
(2), (4) Date: Nov. 23, 2010

(87) PCT Pub. No.: WO2009/133070
PCT Pub. Date: Nov. 5, 2009

(65) Prior Publication Data
US 2011/0060004 A1 Mar. 10, 2011

(30) Foreign Application Priority Data
Apr. 29, 2008 (EP) ..................................... 08155405

(51) Int. Cl.
| C07D 471/04 | (2006.01) |
| A61K 31/437 | (2006.01) |
| A61P 11/00 | (2006.01) |
| A61P 29/00 | (2006.01) |
| A61P 35/00 | (2006.01) |
| A61P 21/00 | (2006.01) |
| A61P 19/00 | (2006.01) |
| A61P 19/10 | (2006.01) |

(52) U.S. Cl.
CPC .................... C07D 471/04 (2013.01)

(58) Field of Classification Search
CPC ........................... A61K 31/437; C07D 471/04
USPC ........................................... 514/303; 546/118
See application file for complete search history.

(56) References Cited

FOREIGN PATENT DOCUMENTS

| EP | 563001 | 9/1993 |
| EP | 0563001 B1 * | 9/1993 |
| WO | WO 01/18000 | 3/2001 |
| WO | WO 2004/013138 | 2/2004 |
| WO | WO 2006024666 A1 * | 3/2006 |
| WO | WO 2008052734 A1 * | 5/2008 |

OTHER PUBLICATIONS

Ten Dijke et. al., Nature Reviews Molecular Cell Biology 8, 857-869, Nov. 2007.*
Rodriguez-Spong et. al., Advanced Drug Delivery Reviews, 2004, 56, 241-274.*
Hong-yu Li, "A Concise Synthesis of Quinazolinone TGF-Beta RI Inhibitor Through One-Pot Three-component Suzuki-Miyaura/Etherification and Imidate-Amid Rearrangement Reactions" *Tetrahedron* 63: 11763-11770, 2007.
Xing Zhou Li, "Synthesis and Biological Evaluation of Novel 2,4,5-triaryl-1 *H*-pyrazol-3(2*H*)-ones as Inhibitors of ALK5" *Chinese Chemical Letters* 19:379-382, 2008.

* cited by examiner

*Primary Examiner* — Kendra D Carter
*Assistant Examiner* — Jason A Deck
(74) *Attorney, Agent, or Firm* — John B. Alexander

(57) ABSTRACT

Compounds of formula (I): in free or salt or solvate form, where X, $R^1$, $R^2$, $R^3$ and $R^4$ have the meanings as indicated in the specification, are useful for treating diseases mediated by the ALK-5 and/or ALK-4 receptor. Pharmaceutical compositions that contain the compounds and processes for preparing the compounds are also described.

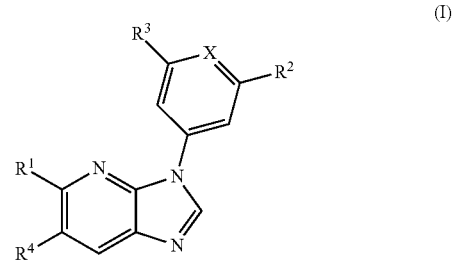

7 Claims, No Drawings

IMIDAZO-PYRIDINE DERIVATIVES AS ACTIVIN-LIKE RECEPTOR KINASE (ALK4 OR ALK5) INHIBITORS

This invention relates to organic compounds and their use as pharmaceuticals, in particular for the treatment of inflammatory or obstructive airways diseases such as pulmonary hypertension, pulmonary fibrosis, liver fibrosis; cancer; muscle diseases such as muscle atrophies and muscle dystrophies, and systemic skeletal disorders such as osteoporosis.

In one aspect, the invention provides a compound of Formula I:

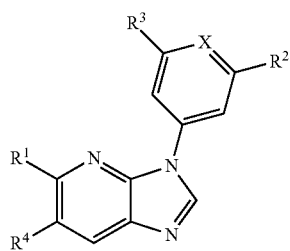

wherein

X is $CR^x$ or N;

$R^1$ is independently selected from H, halo, OH, $C_1$-$C_6$ alkyl, $C_1$-$C_6$ alkoxy, $C_3$-$C_6$ cycloalkyl, $NR^7R^8$ and Z;

$R^2$ is selected from aryl, heterocyclyl, $C_1$-$C_7$ alkyl, $C_3$-$C_{10}$-cycloalkyl, $C_5$-$C_{10}$ cycloalkenyl, $C(O)NR^5R^6$, halo, $C_1$-$C_7$ alkoxy, alkylthio, hydroxyl, $C_1$-$C_7$ alkylcarbonyl, carboxy, carbonyl, cyano and sulfonamide, wherein the alkyl, cycloalkyl, cycloalkenyl, aryl and heterocyclyl groups are optionally substituted by one or more substituents selected from halogen, $C_1$-$C_6$ alkyl and $C_1$-$C_6$ alkoxy;

$R^3$ is selected from H, halo, $NR^{19}R^{20}$ and $OR^{21}$;

$R^4$ is independently selected from H, halogen, aryl and heterocyclyl, wherein the aryl and heterocyclyl groups are optionally substituted by one or more $R^a$ groups and each $R^a$ is independently selected from hydroxyl, carbonyl, aminocarbonyl, $C_1$-$C_7$ alkylaminocarbonyl, amino, $C_1$-$C_7$ alkylamino, $C_1$-$C_7$ alkylthio, sulfonylamino, carbonylamino, $C_1$-$C_7$ alkylcarbonylamino, halo, carboxyl, $C_1$-$C_7$ alkoxy, benzyloxy, $C_1$-$C_7$ alkoxycarbonyl, aminosulfonyl, $C_1$-$C_7$ alkyl, cyano, sulfonyl, sulfanyl, sulfoxide, aryl, heterocyclyl, carbonyloxy, $C_1$-$C_7$ aminoalkyl, $C_1$-$C_7$ alkylamino-$C_1$-$C_7$ alkyl, and when two $R^a$ groups are present, they may be joined together to form a ring system fused to $R^3$, the group $R^a$ itself being optionally substituted by one or more groups selected from hydroxyl, $C_1$-$C_7$ alkyl, aryl, amino, $C_1$-$C_7$ alkylamino, heterocyclyl, cyano, halo, sulfonyl, sulfanyl, sulfoxide, hydroxy-$C_1$-$C_7$ alkyl, $C_1$-$C_7$ alkoxy and $C_1$-$C_7$ alkylamino-$C_1$-$C_7$ alkyl, provided that when $R^4$ is other than H, $R^1$ is H, halo, OH, $C_1$-$C_6$ alkyl, $C_1$-$C_6$ alkoxy or $C_3$-$C_6$ cycloalkyl; and when $R^4$ is H, $R^1$ is halogen, $NR^7R^8$ or Z;

$R^x$ is selected from H, OH and $C_1$-$C_3$ alkoxy;

$R^5$, $R^6$ and $R^7$ are each independently selected from H, $C_1$-$C_6$ alkyl, $C_3$-$C_8$ cycloalkyl and $C_1$-$C_3$ alkyl-$C_3$-$C_8$ cycloalkyl;

$R^8$ is selected from $C_3$-$C_{10}$ cycloalkyl and a 5- or 6-membered heterocyclic group, each optionally substituted by one or more groups selected from $C_1$-$C_6$ alkyl, $C_1$-$C_6$ alkoxy, OH and $C_1$-$C_6$ alkyl substituted by OH or $NH_2$;

Z is selected from 5- or 6-membered heteroaryl and aryl, each being optionally substituted by one or more groups independently selected from $C_1$-$C_6$ alkyl, $C_1$-$C_6$ alkoxy, OH, CN, halo, —C(O)H, —C(O)O$C_1$-$C_6$ alkyl, —C(O)$NR^9R^{10}$, —$(CH_2)_p NR^{11}R^{12}$, —$(CH_2)_n$het, —$NR^{13}C(O)C_1$-$C_6$ alkyl and —$NR^{14}S(O)_2 C_1$-$C_6$ alkyl;

het is a 5- or 6-membered heterocyclic group optionally substituted by one or more groups selected from OH, $C_1$-$C_3$ alkyl and $C_1$-$C_3$ alkoxy;

n and p are each independently 0, 1 or 2;

$R^9$, $R^{11}$, $R^{13}$ and $R^{14}$ are each independently selected from H, $C_1$-$C_6$ alkyl, $C_3$-$C_8$ cycloalkyl and $C_1$-$C_3$ alkyl-$C_3$-$C_8$ cycloalkyl;

$R^{10}$ is selected from H, $C_1$-$C_6$ alkyl, $C_1$-$C_6$ hydroxyalkyl, —$(CH_2)_m NR^{15}R^{16}$ and $C_5$-$C_7$ cycloalkyl optionally substituted by one or more groups selected from OH, $C_1$-$C_3$ alkyl and $C_1$-$C_3$ alkoxy; or $R^9$ and $R^{10}$, together with the nitrogen atom to which they are attached, form a 5- or 6-membered heterocyclic group which optionally contains one or more further heteroatoms selected from N, O and S, the heterocyclic group being optionally substituted by one or more groups selected from OH, $C_1$-$C_3$ alkyl and $C_1$-$C_3$ alkoxy; m is 2 or 3;

$R^{12}$ is selected from H, $C_1$-$C_6$ alkyl and $(CH_2)_q NR^{17}R^{18}$;

q is 2, 3 or 4;

$R^{15}$, $R^{16}$, $R^{17}$ and $R^{18}$ are each independently selected from H, $C_1$-$C_6$ alkyl, $C_3$-$C_8$ cycloalkyl and $C_1$-$C_3$ alkyl-$C_3$-$C_8$ cycloalkyl; or $R^{15}$ and $R^{16}$, together with the nitrogen atom to which they are attached, form a 5- or 6-membered heterocyclic group which optionally contains one or more further heteroatoms selected from N, O and S, the heterocyclic group being optionally substituted by one or more groups selected from OH, $C_1$-$C_3$ alkyl and $C_1$-$C_3$ alkoxy; or $R^{17}$ and $R^{18}$, together with the nitrogen atom to which they are attached, form a 5- or 6-membered heterocyclic group which optionally contains one or more further heteroatoms selected from N, O and S, the heterocyclic group being optionally substituted by one or more groups selected from OH, $C_1$-$C_3$ alkyl and $C_1$-$C_3$ alkoxy; and $R^{19}$, $R^{20}$ and $R^{21}$ are each independently selected from H, $C_1$-$C_6$ alkyl and $C_3$-$C_6$ cycloalkyl; or $R^{19}$ and $R^{20}$, together with the nitrogen atom to which they are attached form a 4-, 5- or 6-membered N-containing heterocyclic group.

In an embodiment of the invention as defined above, $R^4$ is H and $R^1$ is halogen, $NR^7R^8$ or Z. Optionally, $R^4$ is H and $R^1$ is $NR^7R^8$ or Z. Suitably, $R^4$ is H and $R^1$ is $NR^7R^8$.

In an embodiment of the invention as defined anywhere above, $R^2$ is selected from $C(O)NR^5R^6$, $C_1$-$C_6$ alkoxy, $C_5$-$C_6$ cycloalkenyl, halogen, 5- or 6-membered heteroaryl and aryl, wherein the cycloalkenyl, heteroaryl and aryl groups are optionally substituted by one or more groups independently selected from halogen, $C_1$-$C_6$ alkyl and $C_1$-$C_6$ alkoxy. Optionally, $R^2$ is 5- or 6-membered heteroaryl or aryl, each optionally substituted by one or more groups independently selected from halogen, $C_1$-$C_6$ alkyl and $C_1$-$C_6$ alkoxy.

In a further embodiment of the invention as defined anywhere above, $R^3$ is H.

In a further embodiment of the invention as defined anywhere above, $R^4$ is H, phenyl or pyridinyl, wherein the phenyl and pyridinyl groups are optionally substituted by one or more groups independently selected from $C_1$-$C_6$ alkyl, $C_1$-$C_6$ alkoxy, OH, CN, halo, —C(O)H, —C(O)O$C_1$-$C_6$ alkyl, —C(O)N$R^9R^{10}$, —(CH$_2$)$_p$N$R^{11}R^{12}$, —(CH$_2$)$_n$het, —N$R^{13}$C(O)$C_1$-$C_6$ alkyl and —N$R^{14}$S(O)$_2C_1$-$C_6$ alkyl;

$R^9$, $R^{11}$, $R^{13}$ and $R^{14}$ are each independently selected from H and $C_1$-$C_3$ alkyl;

$R^{10}$ is selected from H, $C_1$-$C_6$ alkyl, $C_1$-$C_6$ hydroxyalkyl, —(CH$_2$)$_m$N$R^{15}R^{16}$ and $C_5$-$C_7$ cycloalkyl optionally substituted by one or more groups selected from OH, $C_1$-$C_3$ alkyl and $C_1$-$C_3$ alkoxy; or $R^9$ and $R^{10}$, together with the nitrogen atom to which they are attached, form a 5- or 6-membered heterocyclic group which optionally contains one or more further heteroatoms selected from N, O and S, the heterocyclic group being optionally substituted by one or more groups selected from OH, $C_1$-$C_3$ alkyl and $C_1$-$C_3$ alkoxy; and m is 2 or 3.

In a yet further embodiment of the invention, there is provided a compound of Formula I which is selected from:

4-[3-(2-Furan-3-yl-pyridin-4-yl)-3H-imidazo[4,5-b]pyridin-5-ylamino]-cyclohexanol,
(1SR,2SR)-2-[3-(2-Furan-3-yl-pyridin-4-yl)-3H-imidazo[4,5-b]pyridin-5-ylamino]-cyclohexanol,
{(1SR,2SR)-2-[3-(2-Furan-3-yl-pyridin-4-yl)-3H-imidazo[4,5-b]pyridin-5-ylamino]-cyclohexyl}-methanol,
(1SR,2SR)-3-[3-(2-Furan-3-yl-pyridin-4-yl)-3H-imidazo[4,5-b]pyridin-5-ylamino]-cyclohexanol,
(1SR,3RS)-3-[3-(2-Furan-3-yl-pyridin-4-yl)-3H-imidazo[4,5-b]pyridin-5-ylamino]-cyclohexanol,
(1SR,3SR)-3-[3-(2-Furan-3-yl-pyridin-4-yl)-3H-imidazo[4,5-b]pyridin-5-ylamino]-1-methyl-cyclohexanol,
(1SR, 3RS)-3-{3-[2-(4-Fluorophenyl)-pyridin-4-yl)-3H-imidazo[4,5-b]pyridin-5-ylamino}-cyclohexanol,
(1SR, 3SR)-3-{3-[2-(4-Fluorophenyl)-pyridin-4-yl)-3H-imidazo[4,5-b]pyridin-5-ylamino}-cyclohexanol,
(1SR, 3RS)-3-[3-(2-Furan-3-yl-pyridin-4-yl)-3H-imidazo[4,5-b]pyridin-5-ylamino]-1-methyl-cyclohexanol,
3-[3-(2-Furan-3-yl-pyridin-4-yl)-3H-imidazo[4,5-b]pyridine-5-ylamino]-adamantan-1-ol,
Cyclohexyl-[3-(2-furan-3-yl-pyridin-4-yl)-3H-imidazo[4,5-b]pyridine-5-yl]-amine,
(1SR,3RS)-1-Methyl-3-{3-[2-(1-methyl-1H-pyrazol-3-yl)-pyridine-4-yl}-3H-imidazo[4,5-b]pyridin-5-ylamino]-cyclohexanol,
(1SR,3RS)-3-{3-[2-(3-Methyl-pyrazol-1-yl)pyridine-4-yl]-3H-imidzo[4,5-b]pyridin-5-ylamino}-cyclohexanol,
(1RS,3SR)-3-{3-[2-(3-Methyl-pyrazol-1-yl)pyridine-4-yl]-3H-imidazo[4,5-b]pyridin-5-ylamino}-cyclohexanol,
3-[3-(2-pyrazol-1-yl-pyridin-4-yl)-3H-imidazo[4,5-b]pyridin-5-ylamino]-cyclohexanol,
(1SR,3RS)-1-Methyl-3-{3-(2-pyrazol-1-yl-pyridine-4-yl)-3H-imidazo[4,5-b]pyridin-5-ylamino]-cyclohexanol and
1SR,3RS)-3-[3-(2-Pyrazol-1-yl-pyridine-4-yl)-3H-imidazo[4,5-b]pyridin-5-ylamino]-cyclohexanol.

In the embodiments mentioned herein, where only certain variables are defined, it is intended that the remainder of the variables are as defined in any embodiment herein. Thus, the invention provides for the combination of limited or optional definitions of variables.

The following terms as used herein are intended to have the following meanings:

"Optionally substituted" as used herein means the group referred to can be unsubstituted, or substituted at one or two or three positions by any one or any combination of the radicals listed thereafter.

"Halo" or "halogen" as used herein means fluorine, chlorine, bromine or iodine.

"$C_1$-$C_3$ alkyl", "$C_1$-$C_6$ alkyl", "$C_1$-$C_7$ alkyl" and the like, as used herein, denotes a straight chain or branched alkyl group that contains one to three, six or seven (or the relevant number) carbon atoms and which may be substituted as defined.

"Aryl", as used herein, represents an aromatic carbocyclic ring system having 6 to 15 carbon atoms. It can be monocyclic, bicyclic or tricyclic, and may be optionally substituted as defined. Examples of $C_6$-$C_{15}$-aryl groups include but are not limited to phenyl, phenylene, benzenetriyl, indanyl, naphthyl, naphthylene, naphthalenetriyl and anthracenyl.

"Heterocyclyl" or "heterocyclic" refers to a 4- to 14-membered heterocyclic ring system containing at least one ring heteroatom selected from the group consisting of nitrogen, oxygen and sulphur, which may be saturated, partially saturated or aromatic (i.e. heteroaryl). Examples of 4- to 14-membered heterocyclic groups include but are not limited to furan, azetidine, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, pyridinone, morpholine, triazine, oxazine, tetrahydrofuran, tetrahydrothiophene, tetrahydrothiopyran, tetrahydropyran, 1,4-dioxane, 1,4-oxathiane, indazole, quinoline, indole, thiazole, thiophene, isoquinoline, benzothiophene, benzoxazole, benzisoxazole, benzothiazole, benzisothiazole, benzofuran, dihydrobenzofuran, benzodioxole, benzimidazole or tetrahydronaphthyridine. "Heterocyclyl" or "heterocyclic" also includes bridged heterocyclic groups such as 3-hydroxy-8-aza-bicyclo[3.2.1]oct-8-yl and fused ring systems. The 4- to 14-membered heterocyclic group can be unsubstituted or substituted.

"Heterocyclyl" includes heteroaryl and heterocycloalkyl groups.

"Heteroaryl" is an aromatic ring system containing from 5 to 15 ring atoms one or more of which are heteroatoms selected from O, N or S. Preferably there are one or two heteroatoms. Heteroaryl (heterocyclic aryl) represents, for example: pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl. The heteroaryl group can be substituted or unsubstituted.

"$C_3$-$C_{10}$-cycloalkyl" denotes a fully saturated carbocyclic ring having 3 to 10 ring carbon atoms, for example a monocyclic group such as a cyclopropyl, cyclobutyl, cyclopentyl or cyclohexyl, cycloheptyl, cyclooctyl, cyclononyl or cyclodecyl, or a bicyclic group such as bicycloheptyl or bicyclooctyl. Different numbers of carbon atoms may be specified, with the definition being amended accordingly. The cycloalkyl group can be substituted or unsubstituted.

"$C_5$-$C_{10}$-cycloalkenyl" denotes a partially saturated carbocyclic ring having 5 to 10 ring carbon atoms, for example a monocyclic group such as a cyclopentenyl or cyclohexenyl, cycloheptenyl, cyclooctenyl or cyclononenyl, or a bicyclic group such as bicycloheptenyl or bicyclooctenyl. The ring or ring system may contain more than one carbon-carbon double bond. Different numbers of carbon atoms may be specified, with the definition being amended accordingly. The cycloalkenyl group can be substituted or unsubstituted.

"$C_1$-$C_7$-haloalkyl" as used herein denotes $C_1$-$C_7$-alkyl as hereinbefore defined substituted by one or more halogen atoms, preferably one, two or three halogen atoms. Different numbers of carbon atoms may be specified, with the definition being amended accordingly.

"$C_1$-$C_7$-alkylamino" as used herein denote amino substituted by one or two $C_1$-$C_7$-alkyl groups as hereinbefore defined, which may be the same or different. Different numbers of carbon atoms may be specified, with the definition being amended accordingly.

"$C_1$-$C_7$-alkoxy" as used herein denotes straight chain or branched alkoxy that contains 1 to 7 carbon atoms. Different numbers of carbon atoms may be specified, with the definition being amended accordingly.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

ompounds of formula I that contain a basic centre are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid, hydroiodic acid, nitric acid, sulfuric acid, phosphoric acid; and organic acids, for example aliphatic monocarboxylic acids such as formic acid, acetic acid, trifluoroacetic acid, propionic acid and butyric acid, caprylic acid, dichloroacetic acid, hippuric acid, aliphatic hydroxy acids such as lactic acid, citric acid, tartaric acid or malic acid, gluconic acid, mandelic acid, dicarboxylic acids such as maleic acid or succinic acid, adipic acid, aspartic acid, fumaric acid, glutamic acid, malonic acid, sebacic acid, aromatic carboxylic acids such as benzoic acid, p-chloro-benzoic acid, nicotinic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid, ethanesulfonic acid, ethane-1,2-disulfonic acid, 2-hydroxy-ethanesulfonic acid, (+) camphor-10-sulfonic acid, naphthalene-2-sulfonic acid, naphthalene-1,5-disulfonic acid or p-toluenesulfonic acid. These salts may be prepared from compounds of formula I by known salt-forming procedures. Pharmaceutically acceptable solvates are generally hydrates.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine, arginine, benethamine, benzathine, diethanolamine, 4-(2-hydroxy-ethyl)morpholine,1-(2-hydroxyethyl) pyrrolidine, N-methyl glutamine, piperazine, triethanolamine or tromethamine. These salts may be prepared from compounds of formula I by known salt-forming procedures. Compounds of formula I that contain acidic, e.g. carboxyl, groups may also exist as zwitterions with the quaternary ammonium centre.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Some compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

The invention includes all such forms, in particular the pure isomeric forms. The different isomeric forms may be separated or resolved one from the other by conventional methods, or any given isomer may be obtained by conventional synthetic methods or; by stereospecific or asymmetric syntheses. Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

The invention includes all pharmaceutically acceptable isotopically-labelled compounds of formula I wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^2$H and $^3$H, carbon e.g. $^{11}$C, $^{13}$C and $^{14}$C, chlorine e.g. $^{36}$Cl, fluorine e.g. $^{18}$F, iodine e.g. $^{123}$I and $^{125}$I, nitrogen e.g. $^{13}$N and $^{15}$N, oxygen e.g. $^{15}$O, $^{17}$O and $^{18}$O, and sulfur e.g. $^{35}$S.

Certain isotopically-labelled compounds of formula I, for example those incorporating a radioactive isotope, are useful in drug and/or substrate tissue distribution studies. The radioactive isotopes tritium ($^3$H) and carbon-14 ($^{14}$C) are particularly useful for this purpose in view of their ease of incorporation and ready means of detection. Substitution with heavier isotopes such as deuterium (2H) may afford certain therapeutic advantages that result from greater metabolic stability, for example increased in vivo half-life or reduced dosage requirements, and hence may be preferred in some circumstances. Substitution with positron emitting isotopes, such as $^{11}$C, $^{18}$F, $^{15}$O, and $^{13}$N can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying examples using an appropriate isotopically-labelled reagent in place of the non-labelled reagent previously used.

Pharmaceutically acceptable solvates in accordance with the invention include those wherein the solvent of crystallisation may be isotopically substituted e.g. $D_2O$, $d_6$-acetone or $d_6$-DMSO.

Synthesis

The compounds of the invention may be synthesized by the general synthetic route below, specific examples of which are described in more detail in the Examples.

Scheme 1

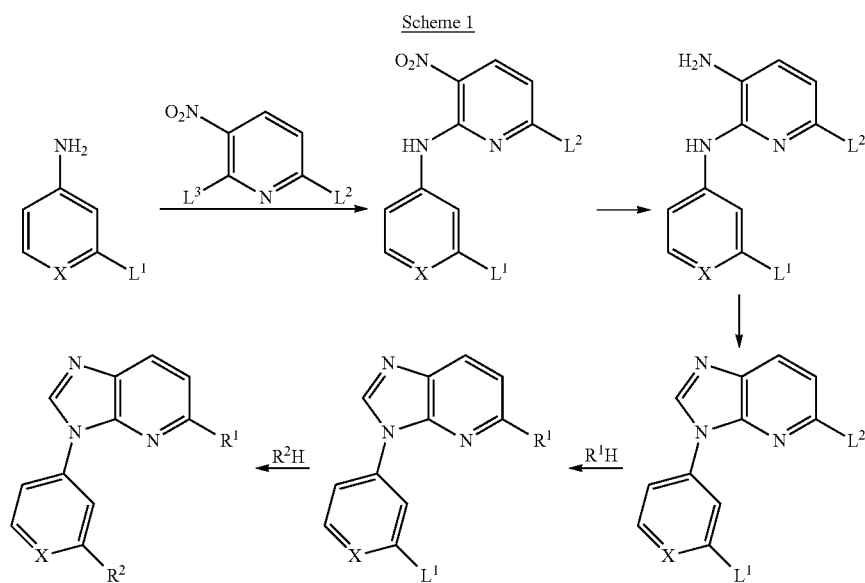

The above general scheme may be used to prepare compounds of Formula I, wherein $R^3$ and $R^4$ are both H. In Scheme 1, $L^1$, $L^2$ and $L^3$ are all appropriate leaving groups, such as, for example, halogen groups. Furthermore, the skilled person will appreciate that alternative reagents to $R^1H$ and $R^2H$ may be used, for example with different leaving groups or using a salt form of the reagent. The desired specific compounds can be prepared by selecting the appropriate starting materials, reactants and reaction conditions.

The starting materials and reagents in the above scheme are all either available commercially or can be prepared following literature precedents.

The above scheme shows the synthesis of compounds of Formula I in which $R^3$ and $R^4$ are both H. However, the skilled person will appreciate that compounds of Formula I where $R^3$ and $R^4$ are other than H can be synthesized using analogous synthetic routes by use of the appropriate starting material, reactants and reaction conditions.

Compounds of Formula I where X is N can be synthesized by use of the appropriate pyridinyl starting material and compounds of Formula I where X is $CR^4$ can be synthesized using analogous synthetic routes by use of the appropriate phenyl reactant in place of the pyridinyl reactant.

The skilled person will appreciate that the order of the last two steps may be reversed. That is to say, $L^1$ can be replaced with $R^2$ before $L^2$ is replaced with $R^1$.

The compounds of formula I can be prepared, e.g., using the reactions and techniques described in detail in the Examples or modifications thereof. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the above reaction scheme can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula I into another compound of formula I. Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5th Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups in Organic Synthesis*, Wiley and Sons (1999).

As a further aspect of the present invention, there is also provided a process for the preparation of compounds of formula I in free or salt or solvate form.

According to a further aspect of the invention there is provided a process of preparing a compound of formula I comprising the step of:

(a) reacting a compound of Formula II

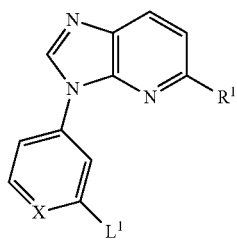

where X and R¹ are as defined anywhere above and L¹ is a suitable leaving group, such as for example a halogen atom, with a compound R²A² where R² is as defined anywhere above and A² is a suitable reactive group, such as for example H, a boronic acid or boronic anhydride; or (b) reacting a compound of Formula III

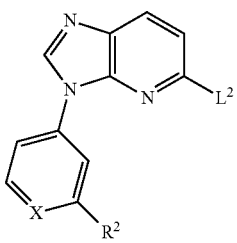

where X and R² are as defined anywhere above and L² is a suitable leaving group, such as for example a halogen atom, with a compound having the formula R¹A¹, where R¹ is as defined anywhere above and A¹ is a suitable reactive group, such as for example H, a boronic acid or boronic anhydride.

In the above process, the term "reactive group" is intended to cover all groups which are able to confer upon R¹ or R² the appropriate reactivity in order for the R¹ or R² to displace L² or L¹ as appropriate. Such reactive groups include, for example, boronic acids and boronic anhydrides in the case of palladium catalysed cross coupling reaction and hydrogen atoms, where the reactant is deprotonated prior to or during the reaction to form a negatively charged group.

The agents of the invention act as activin-like kinase ("ALK")-5 inhibitors. At least many of these compounds also act as ALK-4 inhibitors too.

TGF-β1 is the prototypic member of a family of cytokines including the TGF-βs, activins, inhibins, bone morphogenetic proteins and Mullerian-inhibiting substance, that signal through a family of single transmembrane serine/threonine kinase receptors. These receptors can be divided into two classes, the type I or activin like kinase (ALK) receptors and type II receptors. The ALK receptors are distinguished from the type II receptors in that the ALK receptors (a) lack the serine/threonine rich intracellular tail, (b) possess serine/threonine kinase domains that are very homologous between type I receptors, and (c) share a common sequence motif called the GS domain, consisting of a region rich in glycine and serine residues. The GS domain is at the amino terminal end of the intracellular kinase domain and is critical for activation by the type II receptor. Several studies have shown that TGF-β signalling requires both the ALK and type II receptors. Specifically, the type II receptor phosphorylates the GS domain of the type I receptor for TGF-β, ALK5, in the presence of TGF-β. The ALK5, in turn, phosphorylates the cytoplasmic proteins smad2 and smad3 at two carboxy terminal serines. The phosphorylated smad proteins translocate into the nucleus and activate genes that contribute to the production of extracellular matrix. Therefore, preferred compounds of this invention are selective in that they inhibit the type I receptor.

Activins transduce signals in a manner similar to TGF-β. Activins bind to serine/thereonine kinase, the activin type II receptor (ActRIIB), and the activated type II receptor hyperphosphorylates serine/threonine residues in the GS region of the ALK4.

The activated ALK4 in turn phosphorylates Smad2 and Smad3. The consequent formation of a hetero-Smad complex with Smad4 results in the activin-induced regulation of gene transcription.

Activation of the TGF-β1 axis and expansion of extracellular matrix are early and persistent contributors to the development and progression of chronic renal disease and vascular disease. Border W. A., et al, *N. Engl. J. Med.*, 1994; 331(19), 1286-92. Further, TGF-β1 plays a role in the formation of fibronectin and plasminogen activator inhibitor-1, components of sclerotic deposits, through the action of smad3 phosphorylation by the TGF-β1 receptor ALK5. Zhang Y., et al, *Nature*, 1998; 394(6696), 909-13; Usui T., et al, *Invest. Ophthalmol. Vis. Sci.*, 1998; 39(11), 1981-9.

Progressive fibrosis in the kidney and cardiovascular system is a major cause of suffering and death and an important contributor to the cost of health care. TGF-β1 has been implicated in many renal fibrotic disorders. Border W. A., et al, *N. Engl. J. Med.*, 1994; 331(19),1286-92. TGF-β1 is elevated in acute and chronic glomerulonephritis Yoshioka K., et al, *Lab. Invest.*, 1993; 68(2), 154-63, diabetic nephropathy Yamamoto, T., et al, 1993, *PNAS* 90, 1814-1818., allograft rejection, HIV nephropathy and angiotensin-induced nephropathy Border W. A., et al, *N. Engl. 5 J. Med.*, 1994; 331(19), 1286-92. In these diseases the levels of TGF-β1 expression coincide with the production of extracellular matrix. Three lines of evidence suggest a causal relationship between TGF-β1 and the production of matrix. First, normal glomeruli, mesangial cells and non-renal cells can be induced to produce extracellular-matrix protein and inhibit protease activity by exogenous TGF-β1 in vitro. Second, neutralizing anti-bodies against TGF-β1 can prevent the accumulation of extracellular matrix in nephritic rats. Third, TGF-β1 transgenic mice or in vivo transfection of the TGF-β1 gene into normal rat kidneys resulted in the rapid development of glomerulosclerosis. Kopp J. B., et al, *Lab. Invest.*, 1996; 74(6), 991 1003. Thus, inhibition of TGF-β1 activity is indicated as a therapeutic intervention in chronic renal disease.

TGF-β1 and its receptors are increased in injured blood vessels and are indicated in neointima formation following balloon angioplasty Saltis J., et al, *Clin. Exp. Pharmacol. Physiol.*, 1996; 23(3), 193-200. In addition TGF-β1 is a potent stimulator of smooth muscle cell ("SMC") migration in vitro and migration of SMC in the arterial wall is a contributing factor in the pathogenesis of atherosclerosis and restenosis.

Moreover, in multivariate analysis of the endothelial cell products against total cholesterol, TGF-β receptor ALK5 correlated with total cholesterol (P<0.001) Blann A. D., et al, *Atherosclerosis*, 1996; 120(1-2), 221-6. Furthermore, SMC derived from human atherosclerotic lesions have an increased ALK5/TGF-β type II receptor ratio. Because TGF-β1 is over-expressed in fibroproliferative vascular lesions, receptor-I variant cells would be allowed to grow in a slow, but uncontrolled fashion, while overproducing extracellular matrix components McCaffrey T. A., et al, Jr., *J. Clin.; Invest.*, 1995; 96(6), 2667-75. TGF-β1 was immunolocalized to non-foamy macrophages in atherosclerotic lesions where active matrix synthesis occurs, suggesting that non-foamy macrophages may participate in modulating matrix gene expression in atherosclerotic remodelling via a TGF-β-dependent mechanism. Therefore, inhibiting the action of TGF-β1 on ALK5 is also indicated in atherosclerosis and restenosis.

Liver fibrosis is the result of unbalanced wound healing response to chronic liver injury trigged by a number of agents, such as hepatitis B and hepatitis C virus, alcohol or drugs, and autoimmune diseases. Ultimately, liver fibrosis could lead to life-threatening cirrhosis and liver cancer (see review article by Gressner et al (2006) *J. Cell. Mol. Med.* 2006, 10(1): 76-99).

Several cellular signaling pathways are known to be altered upon chronic liver injury. TGFβ signaling, its receptors and associated Smad-signaling proteins are well documented to be present in cell types involved in fibrogenesis. The circulating levels of TGFβ have been found to be elevated in a number of animal models of fibrotic diseases including liver fibrosis. Transgenic mice with overexpression of TGFβ1 develop fibrosis in multiple organs including liver, kidney, lungs and heart. It is apparent that an elevated TGFβ signaling is involved in all types of fibrotic diseases including liver fibrosis. This notion has been further validated in several studies using TGFβ inhibitors in fibrosis models. TGFβ mediates it signal by binding to two ser/thr kinase receptors, TGFβRII and ALK5. Expressing a dominant negative TGF-βRII showed beneficial effects in a rat model of dimethylnitrosamine induced liver fibrosis (see Qi et al (1999) *Proc. Natl. Acad. Sci.* 96: 2345-9 and Nakamura et al (2000) *Hepatology* 32: 247-55). Inhibiting TGFβ expression using an antisense approach also reduced liver fibrosis induced by bile duct ligation (see Arias et al (2003) BMC *Gastroenterol.* 3: 29). Recently, a small molecule inhibitor of ALK5, GW6604, when given therapeutically to rat, had significant effect in the treatment of dimethylnitrosamine induced liver fibrosis. It is quite remarkable that GW6604 prevented 40% of the death rate and inhibited extracellular matrix deposition by 60%, a key measurement for fibrosis. Importantly, no obvious side effects were noted during the 3 weeks treatment with GW6604 (see De Gouville et al (2005) *Br. J. Pharmacol.* 145: 166-77). Taken together these studies suggest that inhibiting TGF signaling could be an effective treatment for liver fibrotic diseases.

TGF-β1 is also indicated in wound repair. Neutralizing antibodies to TGF-β1 have been used in a number of models to illustrate that inhibition of TGF-β1 signalling is beneficial in restoring function after injury by limiting excessive scar formation during the healing process. For example, neutralizing antibodies to TGF-β1 and TGF-β2 reduced scar formation and improved the cytoarchitecture of the neodermis by reducing the number of monocytes and macrophages as well as decreasing dermal fibronectin and collagen deposition in rats Shah M., *J. Cell. Sci.*, 1995, 108, 985-1002. Moreover, TGF-β antibodies also improve healing of corneal wounds in rabbits Moller-Pedersen T., *Curr. Eye Res.*, 1998, 17, 736-747, and accelerate wound healing of gastric ulcers in the rat, Ernst H., *Gut,* 1996, 39, 172-175. These data strongly suggest that limiting the activity of TGF-β would be beneficial in many tissues and suggest that any disease with chronic elevation of TGF-β would benefit by inhibiting smad2 and smad3 signalling pathways.

TGF-β is also implicated in peritoneal adhesions Sand G. M., et al, *Wound Repair Regeneration,* 1999 November-December, 7(6), 504-510. Therefore, inhibitors of ALK5 would be beneficial in preventing peritoneal and sub-dermal fibrotic adhesions following surgical procedures.

TGF-β also implicated in photoaging of the skin (see Fisher G J. Kang S W. Varani J. Bata-Csorgo Z. Wan Y S. Data S. Voorhees J J., Mechanisms of photoaging and chronological skin ageing, *Archives of Dermatology,* 138(11):1462-1470, 2002 Nov. and Schwartz E. Sapadin A N. Kligman L H. "Ultraviolet B radiation increases steady state mRNA levels for cytokines and integrins in hairless mouse skin-modulation by 25 topical tretinoin", *Archives of Dermatological Research,* 290(3):137-144, 1998 Mar.)

TGF-β signaling is also implicated in the development of pulmonary disorders, in particular pulmonary hypertension and pulmonary fibrosis (see Morrell N W, Yang X, Upton P D, Jourdan K B, Morgan N, Sheares K K, Trembath R C, Altered growth responses of pulmonary artery smooth muscle cells from patients with primary pulmonary hypertension to transforming growth factor-beta(1) and bone morphogenetic proteins. *Circulation.* 2001 Aug. 14; 104(7):790-5. Bhatt N, Baran C P, Allen J, Magro C, Marsh C B., Promising pharmacologic innovations in treating pulmonary fibrosis. *Curr Opin Pharmacol.* 2006 Apr. 28).

TGF-β1 levels are increased in animal models of pulmonary hypertension (Mata-Greenwood E, Meyrick B, Steinhorn R H, Fineman J R, Black S M. Alterations in TGF-beta1 expression in lambs with increased pulmonary blood flow and pulmonary hypertension. *Am. J. Physiol. Lung Cell Mol. Physiol.* 2003 July; 285(1):L209-21). Other studies have suggested that pulmonary endothelial cell-derived TGF-β1 can stimulate the growth of pulmonary vascular smooth muscle cells which may underlie the enhanced muscularisation observed in the pulmonary vasculature of individuals with pulmonary hypertension (Sakao S, Taraseviciene-Stewart L, Wood K, Cool C D, Norbert V F. Apoptosis of pulmonary microvascular endothelial cells stimulates vascular smooth muscle cell growth. *Am. J. Physiol. Lung Cell Mol. Physiol.* 2006 Apr. 14). Therefore, inhibiting the action of TGF-β1 on ALK5 is indicated as a therapeutic intervention in pulmonary hypertension.

Additionally, dys-regulated TGF-β signaling has also been implicated in the development of idiopathic pulmonary fibrosis. Activation of ALK5 results in Smad3-activation and downstream modulation of the expression of genes involved in the fibrotic process such as plasminogen activator inhibitor-1, pro-collagen 3A1, and connective tissue growth factor. The levels of TGF-β1 and its downstream pro-fibrotic mediators have been demonstrated to be up-regulated in bronchoalveolar lavage taken from patients with idiopathic pulmonary fibrosis (Hiwatari N, Shimura S, Yamauchi K, Nara M, Hida W, Shirato K. Significance of elevated procollagen-III-peptide and transforming growth factor-beta levels of bronchoalveolar lavage fluids from idiopathic pulmonary fibrosis patients. *Tohoku J. Exp. Med.* 1997 February; 181(2): 285-95) and in animal models of idiopathic pulmonary fibrosis (Westergren-Thorsson G, Hernnas J, Sarnstrand B, Oldberg A, Heinegard D, Malmstrom A. Altered expression of small proteoglycans, collagen, and transforming growth factor-beta 1 in developing bleomycin-induced pulmonary fibrosis in rats. *J. Clin. Invest.* 1993 August; 92(2):632-7).

Transient over-expression of active TGF-β1 in murine lungs, using adenoviral vector-mediated gene transfer, resulted in progressive pulmonary fibrosis in wild-type mice, whereas no fibrosis was seen in the lungs of Smad3 knockout mice up to 28 days following TGF-β1 challenge (Khalil N, Parekh T V, O'Connor R N, Gold L I. Differential expression of transforming growth factor-beta type I and II receptors by pulmonary cells in bleomycin-induced lung injury: correlation with repair and fibrosis. *Exp. Lung. Res.* 2002 April-May; 28(3):233-50. Thus, inhibition of TGF-β1 activation of ALK5 is also indicated for pulmonary fibrosis.

TGF-beta 1 may also be implicated in tumors and hence the agents of the invention may be useful in the treatment of cancer, including prostate cancer, breast cancer, gastric cancer, angiogenesis, metastasis, tumors, e.g. in the treatment and/or prevention of tumor progression.

Activin signalling and overexpression of activin is linked to pathological disorders that involve extracellular matrix accumulation and fibrosis (e.g., Matsuse, T. et al., *Am. J. Respir Cell Mol. Biol.* 13:17-24 (1995); Inoue, S. et al., *Biochem. Biophys. Res. Conn.* 205:441-448 (1994); Matsuse, T. et al., *Am. J. Pathol.* 148:707-713 (1996); De Bleser et al., *Hepatology* 26:905-912 (1997); Pawlowski, J. E., et al., *J. Clin. Invest.* 100:639-648 (1997); Sugiyama, M. et al., *Gastroenterology* 114:550-558 (1998); Munz, B. et al., EMBO J. 18:5205-5215 (1999)), inflammatory responses (e.g., Rosendahl, A. et al., *Am. J. Respir. Cell Mol. Biol.* 25:60-68 (2001), cachexia or wasting (Matzuk7 M. M. et al., *Proc. Natl. Acad. Sci. USA* 91:8817-8821 (1994); Coerver, K. A. et al., *Mol. Endocrinol.* 10:531 543 (1996); Cipriano, S. C. et al., *Endocrinology* 141:2319-2327 (2000)), diseases or pathological responses in the central nervous system (e.g., Logan, A. et al., *Eur. J. Neurosci.* 11:2367-2374 (1999); Logan, A. et al., *Exp. Neurol.* 159:504-510 (1999); Masliah, E. et al., *Neurochem. Int.* 39:393-400 (2001); De Groot, C. J. A. et al., *J. Neuropathol. Exp. Neural.* 58:174-187 (1999); John, G. R. et al., *Nat. Med.* 8:1115-1121 (2002)) and hypertension (e.g., Dahly, A. J. et al., *Am. J. Physiol. Regul. Integr Comp. Physiol.* 283: R757-767 (2002)). Studies have shown that TGF-β and activin can act synergistically to induce extracellular matrix production (e.g., Sugiyama, M. et al., *Gastroerterology* 114; 550-558 (1998)).

It follows, therefore, that inhibition of ALK5 and/or ALK4 phosphorylation of Smad2 and Smad3 by the agents of the invention can be useful to treat and prevent disorders that involve these signalling pathways.

Activin signaling is also implicated in the development of pulmonary disorders, in particular pulmonary hypertension and pulmonary fibrosis. For example, the expression of activin A in lung samples from patients with interstitial pulmonary fibrosis demonstrated strong expression of activin A on metaplastic epithelium, hyperplastic smooth muscle cells, desquamated cells, and alveolar macrophages. Pulmonary arteries from patients with primary or secondary pulmonary hypertension showed abundant immunoreactive activin A on smooth muscle cells. These findings suggest a potential role for this growth factor, activin A, in the pathogenesis of pulmonary tissue remodelling associated with interstitial pulmonary fibrosis and pulmonary hypertension (Matsuse T, Ikegami A, Ohga E, Hosoi T, Oka T, Kida K, Fukayama M, Inoue S, Nagase T, Ouchi Y, Fukuchi Y. Expression of immunoreactive activin A protein in remodelling lesions associated with interstitial pulmonary fibrosis. *Am. J. Pathol.* 1996 March; 148(3):707-13). An increase in fibroblasts and associated connective tissue is a feature of pulmonary fibrosis and pulmonary hypertension. Activin A has been demonstrated to modulate human lung fibroblast (HFL1) activity, particularly with respect to proliferation and its differentiation into myofibroblast, thus activin A has potential effects on proliferation of lung fibroblast and its differentiation into myofibroblast, and may contribute to structural remodelling observed in pulmonary fibrosis and hypertension (Ohga E, Matsuse T, Teramoto S, Katayama H, Nagase T, Fukuchi Y, Ouchi Y. Effects of activin A on proliferation and differentiation of human lung fibroblasts. *Biochem. Biophys. Res. Commun.* 1996 Nov. 12; 228(2):391-6). The induction of pulmonary fibrosis mediated by bleomycin challenge in rats results in the up-regulated expression of activin A in macrophages infiltrated in the lung, and was detected in fibroblasts accumulated in the fibrotic area. Administration of follistatin, an antagonist of activin signalling to bleomycin-treated rats significantly reduced the number of macrophages and neutrophils in bronchoalveolar lavage and reduced the protein content. Follistatin markedly reduced the number of infiltrating cells, ameliorated the destruction of lung architecture, and attenuated lung fibrosis (Aoki F, Kurabayashi M, Hasegawa Y, Kojima I. Attenuation of bleomycin-induced pulmonary fibrosis by follistatin. *Am. J. Respir. Crit. Care Med.* 2005 Sep. 15; 172(6): 713-20).

Therefore, inhibiting activin signalling via ALK4 inhibition may also be beneficial for the treatment of pulmonary fibrosis and pulmonary hypertension.

It has been demonstrated recently that reduction in TGF-β signalling, through its effector Smad3, enhances the mechanical properties and mineral concentration of the bone matrix, as well as the bone mass, enabling the bone to better resist fracture. These results suggest that reduction of TGF-β signalling could be considered as a therapeutic target to treat bone disorders. (Balooch G, et al. *Proc. Natl. Acad. Sci. USA.* 2005 Dec. 27; 102(52):18813-8). Thus, inhibition of TGF-β1 activation of ALK5 is also indicated for increasing mineral density strength and content of bone and may be utilized to treat a wide variety of conditions, including for example, osteopenia, osteoporosis, fractures and other disorders in which low bone mineral density are a hallmark of the disease.

Having regard to their inhibition of ALK-5 and/or ALK-4 receptors, agents of the invention are useful in the treatment of conditions mediated by the ALK-5 and/or ALK-4 receptors. Treatment in accordance with the invention may be symptomatic or prophylactic.

Therefore according to a further aspect, the invention provides the use of agents of the invention in the preparation of a medicament for treating or preventing a disease or condition mediated by ALK-5 inhibition or ALK-4 inhibition.

Diseases or condition mediated by ALK-5 inhibition or ALK-4 inhibition include glomerulo-nephritis, diabetic nephropathy, lupus nephritis, hypertension-induced nephropathy, renal interstitial fibrosis, renal fibrosis resulting from complications of drug exposure, HIV-associated nephropathy, transplant necropathy, liver fibrosis due to all etiologies, hepatic dysfunction attributable to infections, alcohol-induced hepatitis, disorders of the biliary tree, pulmonary fibrosis, pulmonary hypertension, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub dermal adhesion, scleroderma, fibrosclerosis, progressive systemic sclerosis, dermatomyositis, polymyositis, arthritis, ulcers, impaired neurological function, male erectile dysfunction, Alzheimer's disease, Raynaud's syndrome, fibrotic cancers, tumor metastasis growth, radiation-induced fibrosis, thrombosis, and bone conditions such as osteopenia and osteoporosis, which are associated with increased calcium depletion or resorption or in which stimulation of bone formation and calcium fixation in the bone is desirable.

Diseases or conditions mediated by ALK-5 inhibition in particular include chronic renal disease, acute renal disease, wound healing, arthritis, osteoporosis, kidney disease, congestive heart failure, inflammatory or obstructive airways diseases, pulmonary hypertension, ulcers (including diabetic ulcers, chronic ulcers, gastric ulcers, and duodenal ulcers), ocular disorders, corneal wounds, diabetic nephropathy, impaired neuro-logical function, Alzheimer's disease, atherosclerosis, peritoneal and sub-dermal adhesion, any disease wherein fibrosis is a major component, including, but not limited to kidney fibrosis, lung fibrosis and liver fibrosis, for example, hepatitis B virus (HBV), hepatitis C virus (HCV), alcohol-induced hepatitis, haemochromatosis, primary biliary cirrhosis, restenosis, retroperitoneal fibrosis, mesenteric fibrosis, endometriosis, keloids, cancer, abnormal bone function, inflammatory disorders, scarring and photaging of the skin.

Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include adult/acute respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Preferably the disease or condition mediated by ALK-5 inhibition or ALK-4 inhibition is pulmonary hypertension, pulmonary fibrosis, liver fibrosis, muscular diseases, cancer or osteoporosis.

Pulmonary hypertension to be treated in accordance with the invention includes primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

Pulmonary hypertension to be treated in accordance with the invention is most particularly pulmonary hypertension associated with disorders of the respiratory system and/or hypoxemia, including chronic obstructive pulmonary disease, interstitial lung disease, sleep-disordered breathing, alveolar hypoventilation disorders, chronic exposure to high altitude, neonatal lung disease and alveolar-capillary dysplasia, but especially chronic obstructive pulmonary disease.

Lung fibrosis includes idiopathic pulmonary fibrosis in particular.

Compounds of the present may also be used to treat muscle diseases including muscular atrophies (e.g. disuse), muscular dystrophies (e.g. Duchenne's Muscle Dystrophy, Becker's Muscle Dystrophy, Limb-Girdle Muscle Dystrophy, Facioscapulohumeral Dystrophy), sarcopenia and cachexia.

Treatment of muscular diseases such as muscle atrophies and dystrophies is a largely unmet medical need. There are only few compounds approved for the use in assorted muscle disorders, mainly in the area of cancer-induced and HIV muscle wasting or cachexia, and a few more drugs are used off-label for these indications. In addition, most of these drugs only address the weight loss and do not specifically affect muscular growth and function. There is therefore a need for effective therapies to treat functional impairments associated with muscle diseases related to cachexia (e.g. in cancer, HIV and COPD), disuse atrophy, sarcopenia and dystrophy.

Myostatin, a member of the transforming growth factor $\beta$ (TGF$\beta$) family, is a key negative regulator of skeletal muscle mass. In double-muscle cattle and in a human body with skeletal muscle hypertrophy, different mutations in the myostatin gene were detected (McPherron et al (1997) *Nature* 387:83-90; Schuelke et al (2004) *N. Engl. J. Med.* 350:2682-2688). The important role of myostatin for skeletal muscle growth and disorders was confirmed in a wide variety of in vivo and in vitro studies. For example, muscle-specific overexpression of myostatin in mice causes loss of muscle mass (Reisz-Porszasz et al (2003) AJP-*Endo.* 285:876-888), whereas myostatin null mice have increased skeletal muscle mass and reduced body fat (Lin et al (2002) *Biochem. Bio-* phys. Res. Comm. 291: 701-706). In accordance systemic administration of myostatin induces cachexia (Zimmers et al (2002) Science 296:1486-1488), whereas inhibition of myostatin by, for example, the myostatin neutralizing antibody JA16 increases muscle mass and strength in wildtype and dystrophic mdx mice (Bogdanovich et al (2002) Nature 420: 418-421.2002; Wagner et al (2002) Ann. Neurol. 52: 832-836; Wolfman et al (2003) Proc. Natl. Acad. Sci. 100(26): 15842-15846). In addition, elevated myostatin levels have been observed in both experimental and clinical muscle atrophies such as in patients with Human Immunodeficiency Virus (HIV), cancer or liver cirrhosis as well as in sarcopenia of old age and under glucocorticoid-treatment (Ma et al (2003) Am. J. Physiol. Endocrinol. Metab. 285: E363-371; Gonzales-Cadavid et al (1998) Proc. Natl. Acad. Sci. 95: 14938-14943; see also Reisz-Porszasz et al (2003) AJP-Endo. 285:876-888 and Jespersen et al (2006) Scand. J. Med. Sci. Sports. 16: 74-82). These findings show the high potential of myostatin inhibitors as treatments for muscular atrophies and dystrophies.

The mode of action of myostatin is still under investigation. It is relatively well established that myostatin signals through Smad2/3 (Lee S. J. (2004) Ann. Rev. Dev. Biol. 20: 61-86). Moreover, mature myostatin has been shown to act via activin type IIb and activin receptor like kinase (ALK) receptors in adipocytes (Rebbarpragada et al (2003) Mol. Cell. Biol. 23: 7230-7242). However, respective findings in skeletal muscle cells are not described. Myostatin is believed to inhibit differentiation and cause atrophy via ALK signaling. Moreover, inhibition of ALK signaling promotes skMC differentiation and causes skMC hypertrophy.

Osteoporosis is a systemic skeletal disorder characterized by low bone mass and micro-architectural deterioration of bone tissue, with a consequent increase in bone fragility and susceptibility to fracture. The osteoporotic syndrome is multi faceted, encompassing primary disorders such as postmenopausal or age-related osteoporosis, and secondary conditions that accompany disease states or medications. The mechanical properties and composition of bone matrix, along with bone mass and architecture, are critical determinants of a bone's ability to resist fracture.

Thus in a further aspect the invention includes an agent of the invention for use as a pharmaceutical.

In a yet further aspect the invention includes a method for preventing or treating bone conditions which are associated with increased calcium depletion or resorption or in which stimulation of bone formation and calcium fixation in the bone is desirable in which an effective amount of an agent of the invention, or a pharmaceutically-acceptable and -cleavable ester, or acid addition salt thereof is administered to a patient in need of such treatment.

In a yet further aspect the invention includes a pharmaceutical composition for preventing or treating bone conditions which are associated with increased calcium depletion or resorption or in which stimulation of bone formation and calcium fixation in the bone is desirable comprising an agent of the invention, or a pharmaceutically-acceptable and -cleavable ester, or acid addition salt thereof, in admixture with a pharmaceutically acceptable excipient, diluent or carrier.

In a yet further aspect the invention includes the use of an agent of the invention in the manufacture of a medicament for the treatment or prevention of a bone condition.

The compounds of the Examples herein below generally have $IC_{50}$ values below 10 µM, typically below 1 µM. For instance, the following Examples have the stated $IC_{50}$ values.

| Example | $IC_{50}$ (µM) |
|---|---|
| 1.1 | 0.013 |
| 1.5 | 0.006 |
| 1.9 | 0.318 |
| 1.13 | 0.038 |
| 1.17 | 0.056 |

The kinase activity of ALK5 is assessed by measuring radiolabelled phosphate [33P] incorporation in to the generic substrate, casein. The kinase domain of human ALK5 (amino acids 200-503) is fused to an N-terminal histidine tag. The kinase activity of ALK5 is rendered constitutive via point mutation at amino acid 204 (threonine to aspartate modification, ALK5 T204D) and the kinase construct is engineered to be expressed from a baculovirus expression construct in insect cells. The purified, recombinantly-expressed histidine-tagged ALK5 T204D protein is dissolved at 5.4 mg/ml in 50 mM Tris-HCl pH 8.0, 150 mM NaCl, 5 mM DTT. ALK5 T204D is dissolved to 2.5 µg/ml in assay buffer (Assay buffer: 20 mM Tris-HCl pH 7.4, 10 mM $MgCl_2$, 2 mM $MnCl_2$) on the day of use.

Test compounds and reference compounds are dissolved in assay buffer without DTT containing 5% (v/v) DMSO. Stock solutions of test and reference compounds are diluted in assay buffer with DTT (1.25 mM) containing 4.5% (v/v) DMSO. 10 µl of test or reference compound are added to the appropriate wells of 96 well U-bottomed plate. Total enzyme activity is determined by measuring ALK5 T204D activity in the absence of ALK5 kinase inhibitor reference compounds. Non-specific binding (NSB) is determined by measuring the activity of ALK5 T204D in the presence of ALK5 kinase inhibitor reference compounds. 10 µl of dephosphorylated casein stock solution (dephosphorylated casein is dissolved in $ddH_2O$ at 20 mg/ml) is added per well (200 µg/well final assay concentration). 20 µl of ALK5 T204D (2.5 µg/ml solution) is added per well (50 ng/well final assay concentration). The plates are left to incubate at room temperature for 10 minutes.

10 µl of ATP mix is added to the well to initiate the reaction (0.66 nM [$^{33}$P]ATP/1 µM unlabelled ATP/well final assay concentration). The ATP mix is prepared as follows, unlabelled ATP (3 mM) is dissolved in ddH2O and pH adjusted to 7.4. The stock concentration of [$^{33}$P]ATP is 10 µCi/µl. The appropriate volume of [$^{33}$P]ATP is added to unlabelled ATP solution such that the final assay concentration per well is 0.1 µCi. Following addition of the ATP mix, the plates are incubated at room temperature for 50 minutes. The kinase reaction is terminated by the addition of 50 µL Stop Buffer (20 mM Tris-HCl pH 7.4, 10 mM EDTA).

75 µl/well from the reaction plate is transferred to a Multiscreen-IP plate (MultiScreen-IP plates are prepared by added 50 µL of 70% (v/v) ethanol per well and incubated for 5 minutes at room temperature. The ethanol is removed by aspiration via a MultiScreen HTS Vaccum Manifold unit (Millipore, Cat no: MSVMHT500). The plates are washed twice by adding 200 µl/well $ddH_2O$). The MultiScreen-IP plate is incubated at room temperature for 30 minutes to allowing binding of casein to the plate. The MultiScreen-IP plates are washed three times by adding 200 µl/well 100 mM phosphoric acid solution and the gasket is carefully removed from the back of the MultiScreen-IP plate and the plate dried in the oven for 30 minutes. The MultiScreen-IP plate is backsealed, 50 µL of MICROSCINT™20 is added, then the plates are topsealed and radiolabelled casein detected and quantified on a TOPCOUNT™ plate-reader using the $^{33}$P scintillation protocol.

The agents of the invention are also useful as co-therapeutic agents for use in combination with other drug substances such as anti-inflammatory, bronchodilatory, antihistamine, decongestant or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with one or more other drug substances in a fixed pharmaceutical composition or it may be administered separately, before, simultaneously with or after the other drug substance(s).

Such anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 [Novartis] (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935, WO 04/26248 and WO 05/05452; LTB4 antagonists such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700 and WO 04/108720; LTD4 antagonists such as montelukast, pranlukast, zafirlukast, accolate, SR2640, Wy-48,252, ICI 198615, MK-571, LY-171883, Ro 24-5913 and L-648051; Dopamine receptor agonists such as cabergoline, bromocriptine, ropinirole and 4-hydroxy-7-[2-[[2-[[3-(2-phenylethoxy)-propyl]sulfonyl]ethyl]amino]ethyl]-2(3H)-benzothiazolone and pharmaceutically acceptable salts thereof (the hydrochloride being VIOZAN®—AstraZeneca); PDE4 inhibitors such as cilomilast (AIRFLO® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), GRC 3886 (Oglemilast, Glenmark), WO 92/19594, WO 93/19749, WO 93/19750, WO 93/19751, WO 99/16766, WO 01/13953, WO 03/104204, WO 03/104205, WO 04/000814, WO 04/000839 and WO 04/005258 (Merck), WO 04018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607, WO 04/037805, WO 04/063197, WO 04/103998, WO 04/111044, WO 05012252, WO 05012253, WO 05/013995, WO 05/030212, WO 05/030725, WO 05/087744, WO 05/087745, WO 05/087749 and WO 05/090345 as well as those described in WO 98/18796 and WO 03/39544. A2a agonists such as those described in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; and A2b antagonists such as those described in WO 02/42298 and WO 03/042214.

Such bronchodilatory drugs include beta-2 adrenoceptor agonists. Suitable beta-2 adrenoceptor agonists include albuterol (salbutamol), metaproterenol, terbutaline, salmeterol, fenoterol, procaterol, and especially, formoterol, carmoterol, GSK159797 and pharmaceutically acceptable salts thereof, and compounds (in free or salt or solvate form) of formula I of WO 0075114, which document is incorporated herein by reference, preferably compounds of the Examples thereof, especially a compound of formula

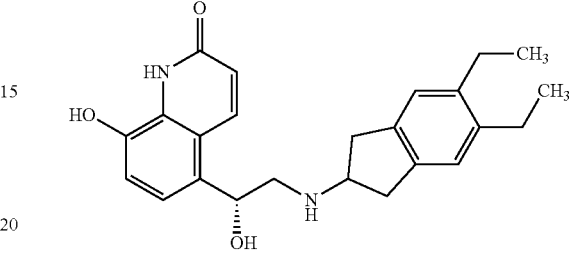

and pharmaceutically acceptable salts thereof, as well as compounds (in free or salt or solvate form) of formula I of WO 04/16601 or of formula I of WO 04/087142. Further suitable β-2-adrenoreceptor agonists include compounds, such as those described in and also compounds of EP 147719, EP 1440966, EP 1460064, EP 1477167, EP 1574501, JP 05025045, JP 2005187357, US 2002/0055651, US 2004/0242622, US 2004/0229904, US 2005/0133417, US 2005/5159448, US 2005/5159448, US 2005/171147, US 2005/182091, US 2005/182092, US 2005/209227, US 2005/256115, US 2005/277632, US 2005/272769, US 2005/239778, US 2005/215542, US 2005/215590, US 2006/19991, US 2006/58530, WO 93/18007, WO 99/64035, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, WO 04/087142, WO 04/89892, WO 04/108675, WO 04/108676, WO 05/33121, WO 05/40103, WO 05/44787, WO 05/58867, WO 05/65650, WO 05/66140, WO 05/70908, WO 05/74924, WO 05/77361, WO 05/90288, WO 05/92860, WO 05/92887, WO 05/90287, WO 05/95328, WO 05/102350, WO 06/56471, WO 06/74897 or WO 06/8173.

Such bronchodilatory drugs also include other anticholinergic or antimuscarinic agents, in particular ipratropium bromide, oxitropium bromide, tiotropium salts, glycopyrrolate, CHF 4226 (Chiesi) and SVT-40776, but also those described in EP 424021, U.S. Pat. No. 3,714,357, U.S. Pat. No. 5,171, 744, US 2005/171147, US 2005/182091, WO 01/04118, WO 02/00652, WO 02/51841, WO 02/53564, WO 03/00840, WO 03/33495, WO 03/53966, WO 03/87094, WO 04/18422, WO 04/05285, WO 04/96800, WO 05/77361 and WO 06/48225.

Suitable dual anti-inflammatory and bronchodilatory drugs include dual beta-2 adrenoceptor agonist/muscarinic antagonists such as those disclosed in US 2004/0167167, US 2004/0242622, US 2005/182092, US 2005/256114, US 2006/35933, WO 04/74246, WO 04/74812, WO 04/89892 and WO 06/23475.

Suitable antihistamine drug substances include cetirizine hydrochloride, levocetirizine, acetaminophen, clemastine fumarate, promethazine, loratidine, desloratidine, diphenhydramine and fexofenadine hydrochloride, activastine, astemizole, azelastine, dimetinden, ebastine, epinastine, levocabastine, mizolastine and tefenadine as well as those disclosed in WO 03/099807, WO 04/026841 and JP 2004107299.

According to a further embodiment of the invention, the agents of the Invention may be employed as adjunct or adjuvant to other therapy, e.g. a therapy using a bone resorption inhibitor, for example as in osteoporosis therapy, in particular a therapy employing calcium, a ealeitonin or an analogue or derivative thereof, e.g. salmon, eel or human calcitonin, a steroid hormone, e.g. an estrogen, a partial estrogen agonist or estrogen-gestagen combination, a SERM (Selective Estrogen Receptor Modulator) e.g. raloxifene, lasofoxifene, TSE-424, FC1271, Tibolone (Livial A), vitamin D or an analog thereof or PTH, a PTH fragment or a PTH derivative e.g. PTH (1-84), PTH (1-34), PTH (1-36), PTH (1-38), PTH (1-31) NH2 or PTS 893.

In accordance with the foregoing, the present invention also provides a method for the treatment of an obstructive or inflammatory airways disease which comprises administering to a subject, particularly a human subject, in need thereof an agent of the invention, or a pharmaceutically acceptable salt or solvate thereof, as hereinbefore described. In another aspect, the invention provides an agent of the invention, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases. In particular, the agents of the invention may be delivered as an inhalable formulation for the treatment of COPD and asthma.

In a further aspect, the invention also provides a pharmaceutical composition comprising an agent of the invention in free form or in the form of a pharmaceutically acceptable salt or solvate thereof, optionally together with a pharmaceutically acceptable diluent or carrier therefor. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

Where the inhalable form of the active ingredient is an aerosol composition, the inhalation device may be an aerosol vial provided with a valve adapted to deliver a metered dose, such as 10 to 100 μl, e.g. 25 to 50 μl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 μl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042, WO 97/20589 (including the CERTIHALER™ device), WO 97/30743 (including the TWISTHALER™ device) and WO 05/37353 (including the GYROHALER™ device).

The invention also includes (A) an agent of the invention in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The invention is illustrated by the following Examples.

EXAMPLES

Example compounds of the present invention include compounds of formula Ia

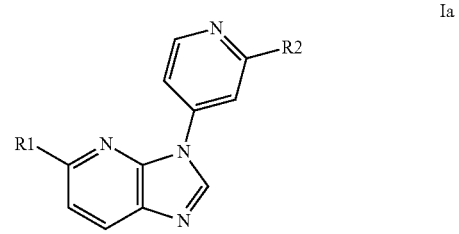

which are shown in Table 1 below, the method of preparation being described hereinafter.

TABLE 1
| Ex. | R¹ | R² | [M + H]⁺ |
|---|---|---|---|
| 1.1 | 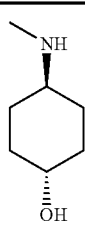 | 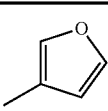 | 376.1 |
| 1.2 | 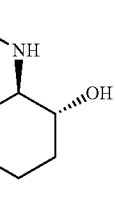 | 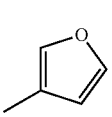 | 375.9 |
| 1.3 | 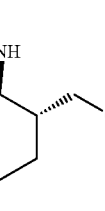 | 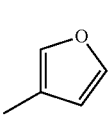 | 390.4 |
| 1.4 | 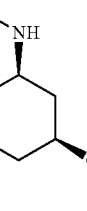 | 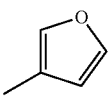 | 376 |
| 1.5 | 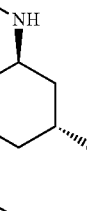 | 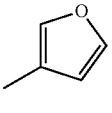 | 376 |
| 1.6 | 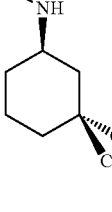 | 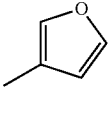 | 389 |
| 1.7 | 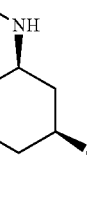 | 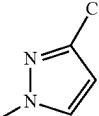 | 390 |
| 1.8 | 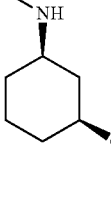 | 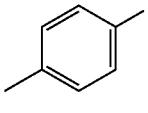 | 404 |
| 1.9 | 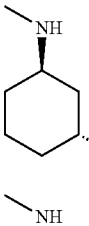 | 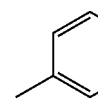 | 404 |
| 1.10 | 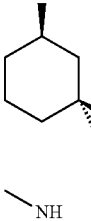 | 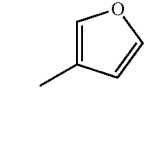 | 390 |
| 1.11 | 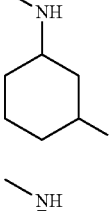 | 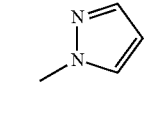 | 376 |
| 1.12 | 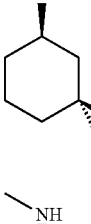 | 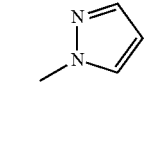 | 390 |
| 1.13 | 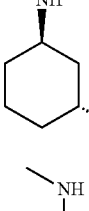 | 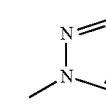 | 390 |
| 1.14 |  | 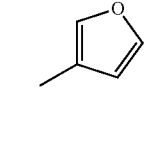 | 428 |
| 1.15 | 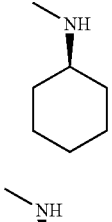 | 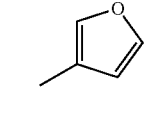 | 360 |
| 1.16 | 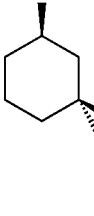 | 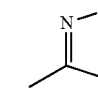 | 404 |

TABLE 1-continued

| Ex. | R¹ | R² | [M + H]⁺ |
|---|---|---|---|
| 1.17 | (trans-3-aminocyclohexanol with NH-methyl, OH) | 1-methyl-pyrazol-3-yl | 376 |

Referring to the examples that follow, compounds of the preferred embodiments are synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

General Conditions:

Mass spectra are run on LCMS systems using electrospray ionization. These are either Agilent 1100 HPLC/Micromass Platform Mass Spectrometer combinations or Waters Acquity HPLC with SQD Mass Spectrometer. [M+H]⁺ refers to mono-isotopic molecular weights.

Abbreviations:

In the experimental section the following abbreviations have been used:
RT room temperature
THF tetrahydrofuran
MeOH methanol
DCM dichloromethane
EtOAc ethyl acetate
EtOH ethanol
LCMS liquid chromatographic mass spectroscopy
HPLC high performance liquid chromatography
IPA Isopropanol
BINAP 2,2'-bis(diphenylphosphino)-1,1'-binapthyl
SCX-2 is strong cation exchange (e.g. ISOLUTE® SCX-2 columns from Biotage)

Preparation of Final Compounds

Example 1.1

4-[3-(2-Furan-3-yl-pyridin-4-yl)-3H-imidazo[4,5-b]pyridin-5-ylamino]-cyclohexanol Step 1: 4-[3-(2-Chloro-pyridin-4-yl)-3H-imidazo[4,5-b]pyridine-5-ylamino]-cyclohexanol A mixture comprising 5-bromo-3-(2-chloro-pyridin-4-yl)-3-H-imidazo[4,5-b]pyridine (Intermediate A)(1 eq, 0.323 mmol, 100 mg), BINAP (0.025 mmol, 40 mg) and Pd₂(dba)₃ (0.0125 mmol, 25 mg) is suspended in dioxane under an inert atmosphere of N2 and heated to 85° C. In a separate flask 4-amino-cyclohexanol (2 eq, 0.647 mmol, 74 mg) and sodium tertbutoxide (2.5 eq, 0.809 mmol, 77 mg) is dissolved in dioxane and warmed to 50° C., before adding to the reaction mixture. The combined mixture was heated for 2 hours. After cooling to room temperature, the mixture is purified by chromatography on silica eluting with 98:2 DCM: ammonia in MeOH to afford the title compound which is used in the next step without further purification; [M+H]⁺310.

Step 2: 4-[3-(2-furan-3-yl-pyridin-4-yl)-3H-imidazo[4,5-b]pyridin-5-ylamino]-cyclohexanol To 4-[3-(2-Chloro-pyridin-4-yl)-3H-imidazo[4,5-b]pyridine-5-ylamino]-cyclohexanol (1 eq, 100 mg, 0.29 mmol), 3-furyl boronic acid (1.05 eq, 0.3 mmol, 34 mg), Na₂CO₃ (2 eq, 0.58 mmol, 62 mg) in EtOH (2 ml) and H₂O (0.7 ml) under inert atmosphere of N₂ is added tetakis(triphenylphosphine) palladium (0.1 eq, 0.029 mmol, 21 mg). The reaction is heated in using microwave radiation at 80° C. for 2 hours. The mixture is diluted with H₂O (5 ml) and extracted with EtOAc. The combined organic portions are washed with brine, dried (MgSO₄) and concentrated in vacuo. The residue is purified by flash chromatography on silica eluting with 0-2.5% MeOH in EtOAc to afford the title compound; [M+H]⁺ 375.

NMR (400 MHz, MeOD): 8.53 (1H, d), 8.48 (1H, s), 8.43 (1H, s), 8.14 (1H, s), 7.95 (1H, dd), 7.61-7.54 (2H, m), 6.96 (1H, s), 6.40 (1H, d), 3.78-3.67 (1H, m), 3.52-3.45 (1H, m), 2.12-2.05 (2H, m), 1.94-1.84 (2H, m) and 1.38-1.12 (4H, m)

The following examples, namely:
Ex. 1.2 (1SR,2SR)-2-[3-(2-Furan-3-yl-pyridin-4-yl)-3H-imidazo[4,5-b]pyridin-5-ylamino]-cyclohexanol,
Ex. 1.3 {(1SR,2SR)-2-[3-(2-Furan-3-yl-pyridin-4-yl)-3H-imidazo[4,5-b]pyridin-5-ylamino]-cyclohexyl}-methanol,
Ex. 1.4 (1SR,2SR)-3-[3-(2-Furan-3-yl-pyridin-4-yl)-3H-imidazo[4,5-b]pyridin-5-ylamino]-cyclohexanol,
Ex 1.5 (1SR, 3RS)-3-[3-(2-Furan-3-yl-pyridin-4-yl)-3H-imidazo[4,5-b]pyridin-5-ylamino]-cyclohexanol,
Ex 1.6 (1SR, 3SR)-3-[3-(2-Furan-3-yl-pyridin-4-yl)-3H-imidazo[4,5-b]pyridin-5-ylamino]-1-methyl-cyclohexanol,
Ex. 1.8 (1SR, 3RS)-3-{3-[2-(4-Fluorophenyl)-pyridin-4-yl)-3H-imidazo[4,5-b]pyridin-5-ylamino}-cyclohexanol,
Ex. 1.9 (1SR, 3SR)-3-{3-[2-(4-Fluorophenyl)-pyridin-4-yl)-3H-imidazo[4,5-b]pyridin-5-ylamino}-cyclohexanol,
Ex. 1.10 (1SR, 3RS)-3-[3-(2-Furan-3-yl-pyridin-4-yl)-3H-imidazo[4,5-b]pyridin-5-ylamino]-1-methyl-cyclohexanol,
Ex 1.14 3-[3-(2-Furan-3-yl-pyridin-4-yl)-3H-imidazo[4,5-b]pyridine-5-ylamino]-adamantan-1-ol,
Ex 1.15 Cyclohexyl-[3-(2-furan-3-yl-pyridin-4-yl)-3H-imidazo[4,5-b]pyridine-5-yl]-amine and
Ex 1.16 (1SR,3RS)-1-Methyl-3-{3-[2-(1-methyl-1H-pyrazol-3-yl)-pyridine-4-yl]-3H-imidazo[4,5-b]pyridin-5-ylamino}-cyclohexanol
are prepared from 5-bromo-3-(2-chloro-pyridin-4-yl)-3-H-imidazo[4,5-b]pyridine (Intermediate A) analogously to Example 1.1 by replacing 4-amino-cyclohexanol with the appropriate amine in step 1 and 3-furan-2-yl boronic acid with the appropriate boronic acid in step 2.

Example 1.13

(1SR,3RS)-3-{3-[2-(3-Methyl-pyrazol-1-yl)pyridine-4-yl]-3H-imidzo[4,5-b]pyridin-5-ylamino}-cyclohexanol Step 1: (1SR,3SR)-3-[3-(2-chloro-pryidin-4-yl)-3H-imidazo[4,5-b]pyridine-5-yl aminocyclohexanol 5-Bromo-3-(2-chloro-pyridin-4-yl)-3-H-imidazo[4,5-b]pyridine (Intermediate A)(1 eq, 0.323 mmol, 100 mg), BINAP (0.025 mmol, 40 mg) and Pd$_2$(dba)$_3$ (0.0125 mmol, 25 mg) are suspended in dioxane under an inert atmosphere of N2 and heated to 85° C. In a separate flask (1SR,3SR)-3-aminocyclohexanol (2 eq, 0.647 mmol, 83 mg) and sodium tertbutoxide (2.5 eq, 0.809 mmol, 77 mg) is dissolved in dioxane and warmed to 50° C. Once at temperature mixture is added to the reaction mixture and heated for 2 hours. After cooling to room temperature, the mixture is purified by chromatography on silica eluting with 98:2 DCM: 2M ammonia in MeOH to afford the title compound which is used in the next step without further purification; [M+H]$^+$ 310.

Step 2: (1SR,3SR)-3-{3-[2-(3-Methyl-pyrazol-1-yl)pyridine-4-yl]-3H-imidzo[4,5-b]pyridin-5-ylamino}-cyclohexanol A mixture comprising 3-[3-(2-chloro-pryidin-4-dazo[4,5-b]pyridine-5-yl hexanol (1 eq, 0.12 mmol, 40 mg), 3-methylpyrazole (5 eq, 0.73 mmol, 50 mg) and cesium carbonate (3 eq, 0.368 mmol, 119 mg) in DMF (2 ml) is heated using microwave radiation at 145° C. for 3 hours. After cooling to room temperature, the mixture is loaded onto a SCX-2 cartridge eluting with MeOH followed by 2M NH$_3$ in MeOH. The methanolic ammonia fractions are concentrated in vacuo and the resulting oil is purified by reverse phase column chromatography (ISOLUTE C18, 0-100% acetonitrile in) and the appropriate fractions are combined and concentrated in vacuo to afford the title compound; [M+H]$^+$=390.

NMR (400 MHz, MeOD), 8.96 (1H, s), 8.89 (1H, s), 8.58-8.55 (2H, m), 7.93 (1H, dd), 7.79 (1H, d), 6.65 (1 h, d), 6.40 (1H, s), 4.02 (1H, ddd), 3.71 (1H, ddd), 2.42 (3H, s), 2.42-2.32 (1H, m), 2.17-2.09 (1H, m), 1.97-1.91 (1H, m), 1.86-1.78 (1H, m), 1.47-1.38 (1H, m) and 1-29-1.15 (3H, m)

The following examples, namely:

Ex. 1.7 (1RS,3SR)-3-{3-[2-(3-Methyl-pyrazol-1-yl)pyridine-4-yl]-3H-imidazo[4,5-b]pyridin-5-ylamino}-cyclohexanol, Ex 1.11 3-[3-(2-Pyrazol-1-yl-pyridin-4-yl)-3H-imidazo[4,5-b]pyridin-5-ylamino]-cyclohexanol, Ex. 1.12 (1SR,3RS)-1-Methyl-3-{3-(2-pyrazol-1-yl-pyridine-4-yl)-3H-imidazo[4,5-b]pyridin-5-ylamino}-cyclohexanol and Ex. 1.17 (1SR,3RS)-3-[3-(2-Pyrazol-1-yl-pyridine-4-yl)-3H-imidazo[4,5-b]pyridin-5-ylamino]-cyclohexanol are prepared from 5-bromo-3-(2-chloro-pyridin-4-yl)-3-H-imidazo[4,5-b]pyridine (Intermediate A) analogously to Example 1.13 by replacing (1SR,3RS)-3-aminocyclohexanol with the appropriate amine in step 1 and 3-methylpyrazole with the appropriate heterocycle in step 2.

Preparation of Intermediate Compounds

Intermediate A

5-Bromo-3-(2-chloro-pyridin-4-yl)-3-H-imidazo[4,5-b]pyridine

Step 1: (6-Bromo-3-nitro-pyridin-2-yl)-(2-chloro-pyridin-4-yl)-amine

2-Chloro-pyridin-4-ylamine (1 eq, 6.6 mmol, 850 mg) and 2,6-dibromo-3-nitro pyridine (2 eq, 13.2 mmol, 3.85 g) are dissolved in IPA (15 ml) and heated using microwave radiation at 150° C. for 6 hours. After cooling to room temperature, triethylamine (1 eq) is added and reaction mixture is stirred for 1 hour. The majority of solvent is removed in vacuo and the residue is diluted using 6% DCM in iso-hexane (75 ml).

The solvent is decanted off and the process repeated 3 times. The resulting brown solid is dissolved in DCM and excess amine is scavenged using SCX-2 resin (6 g) and discarded. The solid is triturated in hexane, DCM and IPA (50 ml of a 58:40:2 mixture) and the resulting yellow solid is collected by filtration. The solid is dissolved in DCM and washed with water. The organic portion is dried (MgSO$_4$) and concentrated in vacuo to afford the title compound; [M+H]$^+$ 330.

Step 2: 6-Bromo-N*2*-(2-chloro-pyridin-4-yl)-pyridine-2,3-diamine (6-Bromo-3-nitro-pyridin-2-yl)-(2-chloro-pyridin-4-yl) amine (step 1) (1 eq, 0.303 mmol, 100 mg) is dissolved in MeOH/THF (6 ml of a 1:1 mixture) and stirred for 5 minutes at RT. Zinc (22 eq, 6.6 mmol 350 mg) is added and the reaction mixture is stirred for a further 20 minutes. Saturated aqueous ammonium chloride (0.8 ml) is added to the reaction mixture and stirring continued at room temperature for 30 minutes. The mixture is filtered through CELITE® and the filtrate is diluted with water (10 ml) and extracted with EtOAc (2×10 ml). The organic portions are combined, dried (MgSO$_4$) and concentrated in vacuo to afford the title compound; [M+H]$^+$300.

Step 3: 5-Bromo-3-(2-chloro-pyridin-4-yl)-3-H-imidazo[4,5-b]pyridine

6-Bromo-N*2*-(2-chloro-pyridin-4-yl)-pyridine-2,3-diamine (step 2)(1 eq, 1.22 mmol, 634 mg) is dissolved in EtOH (15 mL) and treated formamidine acetate (5 eq, 6.105 mmol, 634 mg). The reaction is heated at reflux for 3 hours allowed to cool to room temperature. The mixture is diluted with saturated aqueous sodium bicarbonate and extracted with EtOAc (3×10 ml). The organic portions are combined, dried (MgSO$_4$) and concentrated in vacuo. Purification of the residue by flash chromatography on silica eluting at 5-10% EtOAc in hexane affords the title compound; [M+H]$^+$=310.

The invention claimed is:
1. A compound of Formula I,

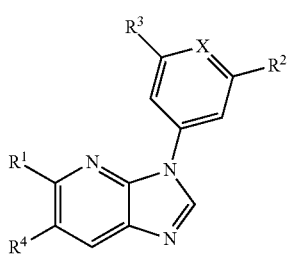

or hydrates or pharmaceutically acceptable salts thereof, wherein

X is CR$^x$ or N;

R$^1$ is NR$^7$R$^8$;

R$^2$ is selected from aryl, heterocyclyl, C$_1$-C$_7$ alkyl, C$_3$-C$_{10}$-cycloalkyl, C$_5$-C$_{10}$ cycloalkenyl, C(O)NR$^5$R$^6$, halo, C$_1$-C$_7$ alkoxy, alkylthio, hydroxyl, C$_1$-C$_7$ alkylcarbonyl, carboxy, carbonyl, cyano and sulfonamide, wherein the alkyl, cycloalkyl, cycloalkenyl, aryl and heterocyclyl groups are optionally substituted by one or more substituents selected from halogen, C$_1$-C$_6$ alkyl and C$_1$-C$_6$ alkoxy;

R$^3$ is selected from H, halo, NR$^{19}$R$^{20}$ and OR$^{21}$;

$R^4$ is hydrogen;

$R^x$ is selected from H, OH and $C_1$-$C_3$ alkoxy;

$R^5$, $R^6$ and $R^7$ are each independently selected from H, $C_1$-$C_6$ alkyl, $C_3$-$C_8$ cycloalkyl and $C_1$-$C_3$ alkyl-$C_3$-$C_8$ cycloalkyl;

$R^8$ is selected from $C_3$-$C_{10}$ cycloalkyl and a 5- or 6-membered heterocyclic group, each optionally substituted by one or more groups selected from $C_1$-$C_6$alkyl, $C_1$-$C_6$ alkoxy, OH and $C_1$-$C_6$ alkyl substituted by OH or $NH_2$; and $R^{19}$, $R^{20}$ and $R^{21}$ are each independently selected from H, $C_1$-$C_6$ alkyl and $C_3$-$C_6$ cycloalkyl; or $R^{19}$ and $R^{20}$, together with the nitrogen atom to which they are attached form a 4-, 5- or 6-membered N-containing heterocyclic group.

2. A compound according to claim 1, wherein $R^2$ is selected from C(O)$NR^5R^6$, $C_1$-$C_6$ alkoxy, $C_5$-$C_6$ cycloalkenyl, halogen, 5- or 6-membered heteroaryl and aryl, wherein the cycloalkenyl, heteroaryl and aryl groups are optionally substituted by one or more groups independently selected from halogen, $C_1$-$C_6$ alkyl and $C_1$-$C_6$ alkoxy.

3. A compound according to claim 2, wherein $R^2$ is 5- or 6-membered heteroaryl or aryl, each optionally substituted by one or more groups independently selected from halogen, $C_1$-$C_6$ alkyl and $C_1$-$C_6$ alkoxy.

4. A compound according to any preceding claim, wherein $R^3$ is H.

5. A pharmaceutical composition including a compound according to claim 1 and one or more pharmaceutically acceptable excipients, diluents or carriers.

6. The compound of claim 1, which compound is selected from compounds of Formula Ia:

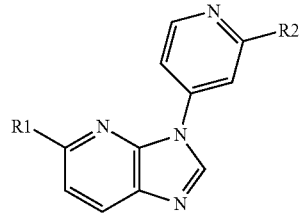

Ia wherein

| $R^1$ | $R^2$ |
|---|---|

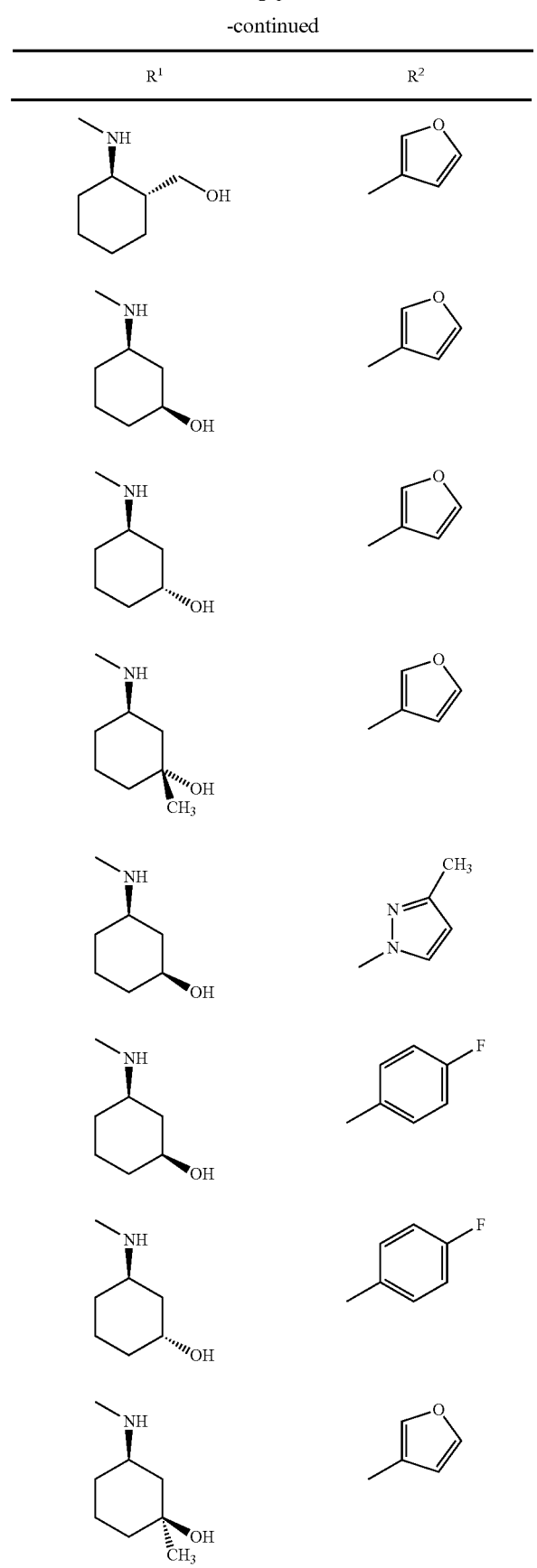

| R¹ | R² |
|---|---|
| 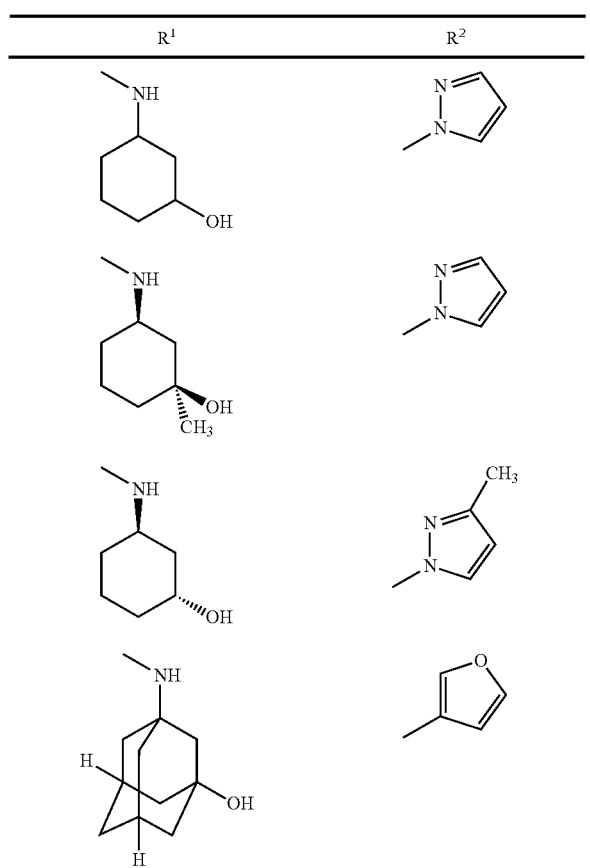 | |
| R¹ | R² |
|---|---|
| 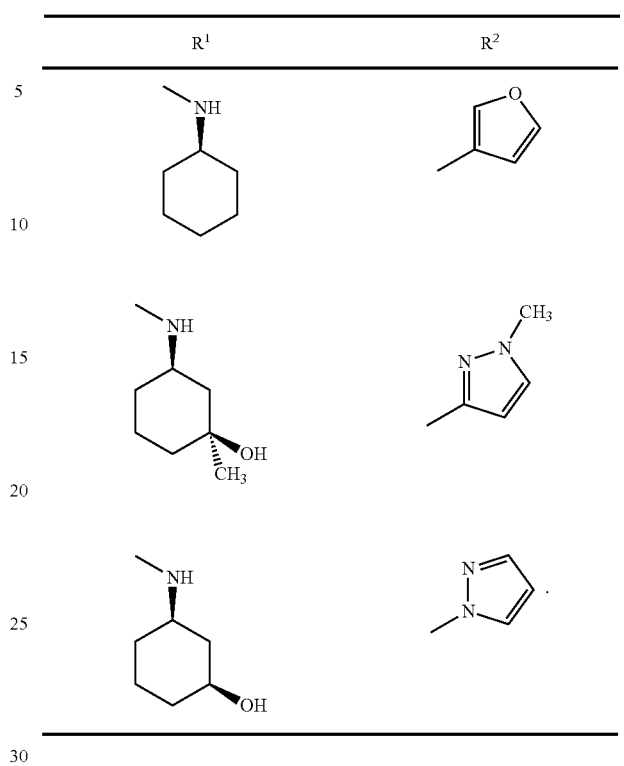 | |
7. A pharmaceutical composition including a compound according to claim 6 and one or more pharmaceutically acceptable excipients.
\* \* \* \* \*